United States Patent
Wang et al.

(10) Patent No.: US 10,542,754 B2
(45) Date of Patent: Jan. 28, 2020

(54) SYNERGISTIC EFFECT OF SPINETORAM AND METHOXYFENOZIDE FOR CONTROL OF STEM BORER ON RICE

(71) Applicants: Peng Wang, Shanghai (CN); Jim X Huang, Zionsville, IN (US); James E. Dripps, Carmel, IN (US); Alisa Y. Yu, Shanghai (CN); Dow AgroSciences LLC, Indianapolis, IN (US)

(72) Inventors: Peng Wang, Shanghai (CN); Jim X Huang, Zionsville, IN (US); James E. Dripps, Carmel, IN (US); Alisa Y. Yu, Shanghai (CN)

(73) Assignee: DOW AGROSCIENCES LLC, Indianapolis, IN (US)

( * ) Notice: Subject to any disclaimer, the term of this patent is extended or adjusted under 35 U.S.C. 154(b) by 76 days.

(21) Appl. No.: 15/319,690

(22) PCT Filed: Jun. 23, 2014

(86) PCT No.: PCT/CN2014/080526
§ 371 (c)(1),
(2) Date: Dec. 16, 2016

(87) PCT Pub. No.: WO2015/196339
PCT Pub. Date: Dec. 30, 2015

(65) Prior Publication Data
US 2017/0142968 A1 May 25, 2017

(51) Int. Cl.
*A01N 43/22* (2006.01)
*A01N 37/18* (2006.01)

(52) U.S. Cl.
CPC ............. *A01N 43/22* (2013.01); *A01N 37/18* (2013.01)

(58) Field of Classification Search
None
See application file for complete search history.

(56) References Cited

FOREIGN PATENT DOCUMENTS

| | | | | |
|---|---|---|---|---|
| CN | 101683072 A | * | 3/2010 | ............. A01N 37/40 |
| CN | 102696603 | | 10/2012 | |
| CN | 103355319 A | * | 10/2013 | ............. A01N 43/22 |
| WO | 2015196339 | | 12/2015 | |

OTHER PUBLICATIONS

McCaffery, A. R. (1998). Resistance to insecticides in heliothine Lepidoptera: a global view. Philosophical Transactions of the Royal Society of London B: Biological Sciences, 353(1376), 1735-1750. (Year: 1998).*
He et al., CN 102696603 A, Oct. 2012, machine translation, Retreived on May 2, 2018 from http://worldwide.espacenet.com (Year: 2012).*
International Search Report, PCTCN2014080526, dated Mar. 16, 2015.

* cited by examiner

*Primary Examiner* — Dale R Miller

(57) ABSTRACT

A method of protecting rice from infestation and attack by pests comprises contacting rice with a pesticidal composition that comprises a synergistically effective amount of spinetoram and methoxyfenozide. The pesticidal composition comprises methoxyfenozide in an amount of at least three parts by weight per one part by weight of spinetoram.

16 Claims, No Drawings

SYNERGISTIC EFFECT OF SPINETORAM AND METHOXYFENOZIDE FOR CONTROL OF STEM BORER ON RICE

CROSS-REFERENCE TO RELATED APPLICATIONS

This is a national phase entry under 35 U.S.C. § 371 of international Patent Application PCT/CN2014/080526, filed Jun. 23, 2014, published in English as International Patent Publication No. WO2015196339 on Dec. 30, 2015.

TECHNICAL FIELD

This disclosure relates to the field of compositions having pesticidal utility against pests in Phyla Nematoda, Arthropoda, and/or Mollusca, processes to produce such compositions and intermediates used in such processes. These compounds may be used, for example, as nematicides, acaricides, miticides, and/or molluscicides.

BACKGROUND

Controlling pest populations is essential to human health, modern agriculture, food storage, and hygiene. There are more than ten thousand species of pests that cause losses in agriculture and the world-wide agricultural losses amount to billions of U.S. dollars each year.

Rice has been reported as the leading food source for humankind, along with wheat. Pests attack all portions of the rice plant and all stages of plant growth. Thus, various pesticides have been used for pest management in rice cultivation. However, there exists a continuous need for new pesticides and for methods of producing and using such new pesticides for pest management.

DETAILED DESCRIPTION

As used herein, the term "synergistic effect" or grammatical variations thereof means and includes a cooperative action encountered in a combination of two or more active compounds in which the combined activity of the two or more active compounds exceeds the sum of the activity of each active compound alone.

The term "synergistically effective amount," as used herein, means and includes an amount of two or more active compounds that provides a synergistic effect defined above.

The term "pesticidally effective amount," as used herein, means and includes an amount of active pesticide that causes an adverse effect to the at least one pest, wherein the adverse effect may include deviations from natural development, killing, regulation, or the like.

As used herein, the term "control" or grammatical variations thereof means and includes regulating the number of living pests or regulating the number of viable eggs of the pests or both.

In one particular embodiment, a method of protecting rice from infestation and attack by pests comprises contacting rice with a pesticidal composition that comprises a synergistically effective amount of spinetoram and methoxyfenozide.

Spinetoram is a known pesticide; see "The Pesticide Manual," 15$^{th}$ Edition, Edited by C D S Tomlin (2009); "Compendium of Pesticide Common Names," available at www.alanwood.net pesticides/index.html.

Methoxyfenozide is a known pesticide; see "The Pesticide Manual." 15$^{th}$ Edition, Edited by C D S Tomlin (2009); "Compendium of Pesticide Common Names," available at www.alanwood.net pesticides/index.html.

Surprisingly, it has been found that the pesticidal composition of the present disclosure has superior pest control on rice at lower levels of the combined concentrations of spinetoram and methoxyfenozide employed than that which may be achieved when spinetoram and methoxyfenozide are applied alone.

TABLE 1

| No. | Range of the Weight Ratio of Spinetoram to Methoxyfenozide |
|---|---|
| 1 | 1:3 to 1:30 |
| 2 | 1:3 to 1:20 |
| 3 | 1:3 to 1:15 |
| 4 | 1:3 to 1:10 |
| 5 | 1:3 to 1:9 |
| 6 | 1:4.5 to 1:9 |
| 7 | 1:4.5 to 1:8 |
| 8 | 1:4.5 to 1:7 |
| 9 | 1:4.5 to 1:6 |
| 10 | 1:4.5 to 1:5.5 |

TABLE 1 shows weight ratios of spinetoram to methoxyfenozide in the synergistic pesticidal compositions of present disclosure. In some embodiments, the weight ratio of spinetoram to methoxyfenozide may be between about 1:3 and about 1:30. In some embodiments, the weight ratio of spinetoram to methoxyfenozide may be between about 1:3 and about 1:20. In some embodiments, the weight ratio of spinetoram to methoxyfenozide may be between about 1:3 and about 1:15. In some embodiments, the weight ratio of spinetoram to methoxyfenozide may be between about 1:3 and about 1:10. In some embodiments, the weight ratio of spinetoram to methoxyfenozide may be between about 1:3 and about 1:9. In some embodiments, the weight ratio of spinetoram to methoxyfenozide may be between about 1:4.5 and about 1:9. In some embodiments, the weight ratio of spinetoram to methoxyfenozide may be between about 1:45 and about 1:8. In some embodiments, the weight ratio of spinetoram to methoxyfenozide may be between about 1:45 and about 1:7. In some embodiments, the weight ratio of spinetoram to methoxyfenozide may be between about 1:4.5 and about 1:6. In some embodiments, the weight ratio of spinetoram to methoxyfenozide may be between about 1:4.5 and about 1:5.5.

TABLE 2

| Methoxyfenozide (Y), Parts by weight | 30.0 | X, Y | | X, Y | | | | | | | X, Y | X, Y |
|---|---|---|---|---|---|---|---|---|---|---|---|---|
| | 27.5 | X, Y | X, Y | | X, Y | | X, Y | X, Y | | X, Y | X, Y | X, Y |
| | 25.5 | X, Y | | X, Y | | X, Y | | | X, Y | | X, Y | | X, Y |
| | 22.5 | X, Y | X, Y | X, Y | X, Y | | | X, Y | X, Y | X, Y | | X, Y | X, Y |
| | 20.0 | | | | | X, Y | | X, Y | | | X, Y | X, Y | X, Y |
| | 17.5 | X, Y | | X, Y | | | X, Y | | X, Y | X, Y | X, Y | | |
| | 15.0 | X, Y | | | | X, Y | X, Y | X, Y | X, Y | X, Y | | | |

TABLE 2-continued

| Y\X | 1.0 | 1.5 | 2.0 | 2.5 | 3.0 | 3.5 | 4.0 | 4.5 | 5.0 | 5.5 | 6.0 | 6.5 |
|---|---|---|---|---|---|---|---|---|---|---|---|---|
| 12.5 | | | | X, Y | | | X, Y | X, Y | X, Y | X, Y | | |
| 10 | X, Y | X, Y | X, Y | X, Y | X, Y | | X, Y | | | | | |
| 7.5 | X, Y | X, Y | X, Y | X, Y | | | | | | | | |
| 5.5 | X, Y | X, Y | | | | | | | | | | |
| 5.0 | X, Y | X, Y | | | | | | | | | | |
| 4.5 | X, Y | X, Y | | | | | | | | | | |
| 4.0 | X, Y | | | | | | | | | | | |
| 3.0 | X, Y | | | | | | | | | | | |

Spinetoram (X), Parts by weight

Weight ratios of spinetoram to methoxyfenozide envisioned to be synergistic pesticidal compositions may be depicted as X:Y; wherein X is the parts by weight of spinetoram and Y is the parts by weight of methoxyfenozide. The numerical range of the parts by weight for X is $0<X\leq6.5$ and the parts by weight for Y is $0<Y\leq30$ as shown graphically in TABLE 2. By way of non-limiting example, the weight ratio of spinetoram to methoxyfenozide may be about 1:5.

Ranges of weight ratios of spinetoram to methoxyfenozide envisioned to be synergistic pesticidal compositions may be depicted as $X_1:Y_1$ to $X_2:Y_2$, wherein X and Y are defined as above. In one particular embodiment, the range of weight ratios may be $X_1:Y_1$ to $X_2:Y_2$, wherein $X_1<Y_1$ and $X_2<Y_2$. By way of non-limiting example, the range of weight ratios of spinetoram to methoxyfenozide may be between about 1:4.5 and about 1:20.

The weight ratio of spinetoram to methoxyfenozide in the synergistic pesticidal composition may be varied and different from those described in TABLE 1 and TABLE 2. One skilled in the art recognizes that the synergistic effective amount of the combination of active compounds may vary accordingly to various prevailing conditions. Non-limiting examples of such prevailing conditions may include the type of pests, the type of crops, the mode of application, the application timing, the weather conditions, the soil conditions, the topographical character, or the like. It is understood that one skilled in the art may readily determine the synergistic effective amount of spinetoram to methoxyfenozide accordingly to the prevailing conditions.

Accordingly, a method of protecting rice from infestation and attack by pests comprises contacting rice with a pesticidal composition that comprises a synergistically effective amount spinetoram and methoxyfenozide. The methoxyfenozide is in an amount of at least 3 parts by weight per 1 part by weight of the spinetoram.

In some embodiments, the method of protecting rice from infestation and attack by pests comprises contacting rice with a pesticidal composition that comprises methoxyfenozide in an amount of at least 4.5 parts by weight per 1 part by weight of spinetoram.

In other embodiments, the pesticidal composition may comprise a synergistically effective amount of spinetoram and methoxyfenozide, and a phytologically-acceptable inert carrier (e.g., solid carrier, or liquid carrier).

In further embodiments, the pesticidal composition may further comprise at least one additive selected from a surfactant, a stabilizer, an emetic agent, a disintegrating agent, an antifoaming agent, a wetting agent, a dispersing agent, a binding agent, dye, filler, or combinations thereof.

In particular embodiments, each of the active compounds, spinetoram and methoxyfenozide, may be formulated separately as a wettable powder, emulsifiable concentrate, aqueous or liquid flowable, suspension concentrate or any one of the conventional formulations used for pesticides, and then tank-mixed in the field with water or other liquid for application as a liquid spray mixture. When desired, the separately formulated pesticides may also be applied sequentially.

In some embodiments, the synergistic pesticidal composition may be formulated into a more concentrated primary composition, which is then diluted with water or other diluent before use. In such embodiments, the synergistic pesticidal composition may further comprise a surface active agent.

In one particular embodiment, the method of protecting a plant from infestation and attack by pests comprises contacting the plant with a pesticidal composition comprising a synergistically effective amount of spinetoram and methoxyfenozide. The methoxyfenozide is in an amount of at least 3 parts by weight per 1 part by weight of the spinetoram.

In other embodiments, the method of protecting a plant from infestation and attack by pests comprises contacting the plant with a pesticidal composition that comprises methoxyfenozide in an amount of at least 4.5 parts by weight per 1 part by weight of spinetoram.

In some embodiments, the pesticidal compositions may be in the form of solid. Non-limiting examples of the solid forms may include powder, dust or granular formulations.

In further embodiments, the pesticidal compositions may be in the form of liquid formulation. Examples of the liquid forms may include, but are not limited to, dispersion, suspension, emulsion or solution in appropriate liquid carrier. In particular embodiments, the synergistic pesticidal compositions may be in the form of liquid dispersion, wherein the synergistic pesticidal compositions may be dispersed in water or other agriculturally suitable liquid carrier.

In certain embodiments, the synergistic pesticidal compositions may be in the form of solution in an appropriate organic solvent. In one embodiment, the spray oils, which are widely used in agricultural chemistry, may be used as the organic solvent for the synergistic pesticidal compositions.

The control of pests may be achieved by applying a pesticidally effective amount of the synergistic pesticidal compositions in form of sprays, topical treatment, gels, seed coatings, microcapsulations, systemic uptake, baits, eartags, boluses, foggers, fumigants aerosols, dusts, or the like.

These disclosed pesticidal compositions may be used, for example, as nematicides, acaricides, miticides, and/or molluscicides.

The pesticidal composition of the present disclosure may be used to control a wide variety of pests. As a non-limiting example, in one or more embodiments, the pesticidal composition may be used to control one or more members of at least one of Phylum Arthropoda, Phylum Nematoda, Subphylum Chelicerata, Subphylum Myriapoda, Subphylum Hexapoda, Class Insecta, Class Arachnida, and Class Symphyla. In at least some embodiments, the method of the present disclosure may be used to control one or more members of at least one of Class Insecta and Class Arachnida.

As a non-limiting example, the method of the present disclosure may be used to control one or more members of at least one of Phylum Arthropoda, Phylum Nematoda, Subphylum Chelicerata, Subphylum Myriapoda, Subphylum Hexapoda, Class Insecta, Class Arachnida, and Class Symphyla. In at least some embodiments, the method of the present disclosure may be used to control one or more members of at least one of Class Insecta and Class Arachnida.

In additional embodiments, the method of the present disclosure may be used to control members of the Order Coleoptera (beetles) including, but not limited to, *Acanthoscelides* spp. (weevils), *Acanthoscelides obtectus* (common bean weevil), *Agrilusplanipennis* (emerald ash borer), *Agriotes* spp. (wireworms), *Anoplophora glabripennis* (Asian longhorned beetle), *Anthonomus* spp. (weevils), *Anthonomus grandis* (boll weevil), *Aphidius* spp., *Apion* spp. (weevils), *Apogonia* spp. (grubs), *Ataenius spretulus* (Black Turfgrass Ataenius), *Atomaria linearis* (pygmy mangold beetle), *Aulacophore* spp., *Bothynoderes punctiventris* (beet root weevil), *Bruchus* spp. (weevils), *Bruchus pisorum* (pea weevil), *Cacoesia* spp., *Callosobruchus maculatus* (southern cow pea weevil), *Carpophilus hemipteras* (dried fruit beetle), *Cassida vittata, Cerosterna* spp., *Cerotoma* spp. (chrysomelids), *Cerotoma trifurcata* (bean leaf beetle), *Ceutorhynchus* spp. (weevils), *Ceutorhynchus assimilis* (cabbage seedpod weevil), *Ceutorhynchus napi* (cabbage curculio), *Chaetocnema* spp. (chrysomelids), *Colaspis* spp. (soil beetles), *Conoderus scalaris, Conoderus stigmosus, Conotrachelus nenuphar* (plum curculio), *Cotinus nitidis* (Green June beetle), *Crioceris asparagi* (asparagus beetle), *Cryptolestes ferrugineus* (rusty grain beetle), *Cryptolestes pusillus* (flat grain beetle), *Cryptolestes turcicus* (Turkish grain beetle), *Ctenicera* spp. (wireworms), *Curculio* spp. (weevils), *Cyclocephala* spp. (grubs), *Cylindrocpturus adspersus* (sunflower stem weevil), *Deporaus marginatus* (mango leaf-cutting weevil), *Dermestes lardarius* (larder beetle), *Dermestes maculates* (hide beetle), *Diabrotica* spp. (chrysomelids), *Epilachna varivestis* (Mexican bean beetle), *Faustinus cubae, Hylobius pales* (pales weevil), *Hypera* spp. (weevils), *Hypera postica* (alfalfa weevil), *Hyperdoes* spp. (Hyperodes weevil), *Hypothenemus hampei* (coffee berry beetle), *Ips* spp. (engravers), *Lasioderma serricorne* (cigarette beetle), *Leptinotarsa decemlineata* (Colorado potato beetle), *Liogenys fuscus, Liogenys suturalis, Lissorhoptrus oryzophilus* (rice water weevil), *Lyctus* spp. (wood beetles/powder post beetles), *Maecolaspis joliveti, Megascelis* spp., *Melanotus communis, Meligethes* spp., *Meligethes aeneus* (blossom beetle), *Melolontha melolontha* (common European cockchafer), *Oberea brevis, Oberea linearis, Oryctes rhinoceros* (date palm beetle), *Oryzaephilus mercator* (merchant grain beetle), *Oryzaephilus surinamensis* (sawtoothed grain beetle), *Otiorhynchus* spp. (weevils), *Oulema melanopus* (cereal leaf beetle), *Oulema oryzae, Pantomorus* spp. (weevils), *Phyllophaga* spp. (May/June beetle), *Phyllophaga cuyabana* (chrysomelids), *Phynchites* spp., *Popillia japonica* (Japanese beetle), *Prostephanus truncates* (larger grain borer), *Rhizopertha dominica* (lesser grain borer), *Rhizotrogus* spp. (European chafer), *Rhynchophorus* spp. (weevils), *Scolytus* spp. (wood beetles), *Shenophorus* spp. (Billbug), *Sitona lineatus* (pea leaf weevil), *Sitophilus* spp. (grain weevils), *Sitophilus granaries* (granary weevil), *Sitophilus oryzae* (rice weevil), *Stegobium paniceum* (drugstore beetle), *Tribolium* spp. (flour beetles), *Tribolium castaneum* (red flour beetle), *Tribolium confusum* (confused flour beetle), *Trogoderma variabile* (warehouse beetle), and *Zabrus tenebioides.*

In other embodiments, the method of the present disclosure may also be used to control members of the Order Dermaptera (earwigs).

In particular embodiments, the method of the present disclosure may be used to control members of the Order Dictyoptera (cockroaches) including, but is not limited to, *Blattella germanica* (German cockroach), *Blatta orientalis* (oriental cockroach), *Parcoblatta pennylvanica, Periplaneta americana* (American cockroach), *Periplaneta australoasiae* (Australian cockroach), *Periplaneta brunnea* (brown cockroach), *Periplaneta fuliginosa* (smokybrown cockroach), *Pyncoselus suninamensis* (Surinam cockroach), and *Supella longipalpa* (brownbanded cockroach).

In further embodiments, the method of the present disclosure may be used to control members of the Order Diptera (true flies) including, but not limited to, *Aedes* spp. (mosquitoes), *Agromyzafrontella* (alfalfa blotch leafminer), *Agromyza* spp. (leaf miner flies), *Anastrepha* spp. (fruit flies), *Anastrepha suspensa* (Caribbean fruit fly), *Anopheles* spp. (mosquitoes), *Bactrocera* spp. (fruit flies), *Bactrocera cucurbitae* (melon fly), *Bactrocera dorsalis* (oriental fruit fly), *Ceratitis* spp. (fruit flies), *Ceratitis capitata* (Mediterranean fruit fly), *Chrysops* spp. (deer flies), *Cochliomyia* spp. (screwworms), *Contarinia* spp. (Gall midges), *Culex* spp. (mosquitoes), *Dasineura* spp. (gall midges), *Dasineura brassicae* (cabbage gall midge), *Delia* spp., *Delia platura* (seedcorn maggot), *Drosophila* spp. (vinegar flies), *Fannia* spp. (filth flies), *Fannia canicularis* (little house fly), *Fannia scalaris* (latrine fly), *Gasterophilus intestinalis* (horse bot fly), *Gracillia per seae, Haematobia irritans* (horn fly), *Hylemyia* spp. (root maggots), *Hypoderma lineatum* (common cattle grub), *Liriomyza* spp. (leafminer flies), *Liriomyza brassica* (serpentine leafminer), *Liriomyza sativae* (vegetable leafminer), *Melophagus ovinus* (sheep ked), *Musca* spp. (muscid flies), *Musca autumnalis* (face fly), *Musca domestica* (house fly), *Oestrus ovis* (sheep bot fly), *Oscinella frit* (frit fly), *Pegomyia betae* (beet leafminer), *Phorbia* spp., *Psila rosae* (carrot rust fly), *Rhagoletis cerasi* (cherry fruit fly), *Rhagoletis pomonella* (apple maggot), *Sitodiplosis mosellana* (orange wheat blossom midge), *Stomoxys calcitrans* (stable fly), *Tabanus* spp. (horse flies), and *Tipula* spp. (crane flies).

In other embodiments, the method of the present disclosure may be used to control members of the Order Hemiptera Sub-order Heteroptera (true bugs) including, but is not limited to, *Acrosternum hilare* (green stink bug), *Blissus leucopterus* (chinch bug), *Bragada hilaris, Calocoris norvegicus* (potato mirid), *Cimex hemipterus* (tropical bed bug), *Cimex lectularius* (bed bug), *Dagbertus fasciatus, Dichelops furcatus, Dysdercus suturellus* (cotton stainer), *Edessa meditabunda, Eurygaster maura* (cereal bug), *Euschistus heros, Euschistus servus* (brown stink bug), *Helopeltis antonii, Helopeltis theivora* (tea blight plantbug), *Lagynotomus* spp. (stink bugs), *Leptocorisa oratorius, Leptocorisa varicornis, Lygus* spp. (plant bugs), *Lygus hesperus* (western tarnished plant bug), *Lygus lineolaris* (tarnished plant bug), *Maconellicoccus hirsutus, Neurocolpus longirostris, Nezara viridula* (southern green stink bug), *Phytocoris* spp. (plant bugs), *Phytocoris californicus, Phytocoris relativus, Piezodorus guildinii* (redbanded stink bug), *Poecilocapsus lineatus* (fourlined plant bug), *Psallus vaccinicola, Pseudacysta perseae, Scaptocoris castanea,* and *Triatoma* spp. (blood-sucking conenose bugs/kissing bugs).

In additional embodiments, the method of the present disclosure may be used to control members of the Order Hemiptera, Sub-orders Auchenorrhyncha (Free-living Hemipterans) and Sternorrhyncha (Plant-parasitic Hemipterans) (aphids, scales, whiteflies, leafhoppers) including, but is not limited to, *Acrythosiphon pisum* (pea aphid), *Adelges* spp. (adelgids), *Aleurodes proletella* (cabbage whitefly), *Aleurodicus disperses, Aleurothrixus floccosus* (woolly whitefly), *Aluacaspis* spp., *Amrasca bigutella bigutella, Aphrophora* spp. (leafhoppers), *Aonidiella aurantii* (California red scale), *Aphis* spp. (aphids), *Aphis gossypii* (cotton aphid), *Aphis pomi* (apple aphid), *Aulacorthum solani* (foxglove aphid), *Bemisia* spp. (whiteflies), *Bemisia argentifolii, Bemisia tabaci* (sweetpotato whitefly), *Brachycolus noxius* (Russian aphid), *Brachycorynella asparagi* (asparagus aphid), *Brevennia rehi, Brevicoryne brassicae* (cabbage aphid), *Ceroplastes* spp. (scales), *Ceroplastes rubens* (red wax scale), *Chionaspis* spp. (scales), *Chrysomphalus* spp. (scales), *Chrysomphalus aonidum* (Florida red scale) *Coccus* spp. (scales), *Coccus pseudomagnoliarum* (citricola scale), *Dysaphis plantaginea* (rosy apple aphid), *Empoasca* spp. (leafhoppers), *Eriosoma lanigerum* (woolly apple aphid), *Icerya purchasi* (cottony cushion scale), *Idioscopus nitidulus* (mango leafhopper), *Laodelphax striatellus* (smaller brown planthopper), *Lepidosaphes* spp., *Macrosiphum* spp., *Macrosiphum euphorbiae* (potato aphid), *Macrosiphum granarium* (English grain aphid), *Macrosiphum rosae* (rose aphid), *Macrosteles quadrilineatus* (aster leafhopper), *Mahanarva frimbiolata, Metopolophium dirhodum* (rose grain aphid), *Mictis longicornis, Myzus* spp., *Myzus persicae* (green peach aphid), *Nephotettix* spp. (leafhoppers), *Nephotettix cinctipes* (green leafhopper), *Nilaparvata lugens* (brown planthopper), *Paratrioza cockerelli* (tomato psyllid), *Parlatoria pergandii* (chaff scale), *Parlatoria ziziphi* (ebony scale), *Peregrinus maidis* (corn delphacid), *Philaenus* spp. (spittlebugs), *Phylloxera vitifoliae* (grape phylloxera), *Physokermes piceae* (spruce bud scale), *Planococcus* spp. (mealybugs), *Planococcus citri* (citrus mealybug), *Planococcus ficus* (grape mealybug), *Pseudococcus* spp. (mealybugs), *Pseudococcus brevipes* (pine apple mealybug), *Quadraspidiotus pemiciosus* (San Jose scale), *Rhopalosiphum* spp. (aphids), *Rhopalosiphum maidis* (corn leaf aphid), *Rhopalosiphum padi* (oat birdcherry aphid), *Saissetia* spp. (scales), *Saissetia oleae* (black scale), *Schizaphis graminum* (greenbug), *Sitobion avenae* (English grain aphid), *Sogatella furcifera* (white-backed planthopper), *Therioaphis* spp. (aphids), *Toumeyella* spp. (scales), *Toxoptera* spp. (aphids), *Trialeurodes* spp. (whiteflies), *Trialeurodes vaporariorum* (greenhouse whitefly), *Trialeurodes abutiloneus* (bandedwing whitefly), *Unaspis* spp. (scales), *Unaspis yanonensis* (arrowhead scale), and *Zulia entreriana*. In at least some embodiments, the method of the present disclosure may be used to control *Myzus persicae*.

In other embodiments, the method of the present disclosure may be used to control members of the Order Hymenoptera (ants, wasps, and sawflies) including, but not limited to, *Acromyrrmex* spp., *Athalia rosae, Atta* spp. (leafcutting ants), *Camponotus* spp. (carpenter ants), *Diprion* spp. (sawflies), *Formica* spp. (ants), *Iridomyrmex humilis* (Argentine ant), *Monomorium* spp., *Monomorium minumum* (little black ant), *Monomorium pharaonis* (Pharaoh ant), *Neodiprion* spp. (sawflies), *Pogonomyrmex* spp. (harvester ants), *Polistes* spp. (paper wasps), *Solenopsis* spp. (fire ants), *Tapoinoma sessile* (odorous house ant), *Tetranomorium* spp. (pavement ants), *Vespula* spp. (yellow jackets), and *Xylocopa* spp. (carpenter bees).

In certain embodiments, the method of the present disclosure may be used to control members of the Order Isoptera (termites) including, but not limited to, *Coptotermes* spp., *Coptotermes curvignathus, Coptotermes frenchii, Coptotermes formosanus* (Formosan subterranean termite), *Comitermes* spp. (nasute termites), *Cryptotermes* spp. (drywood termites), *Heterotermes* spp. (desert subterranean termites), *Heterotermes aureus, Kalotermes* spp. (drywood termites), *Incistitermes* spp. (drywood termites), *Macrotermes* spp. (fungus growing termites), *Marginitermes* spp. (drywood termites), *Microcerotermes* spp. (harvester termites), *Microtermes obesi, Procornitermes* spp., *Reticulitermes* spp. (subterranean termites), *Reticulitermes banyulensis, Reticulitermes grassei, Reticulitermes flavipes* (eastern subterranean termite), *Reticulitermes hageni, Reticulitermes hesperus* (western subterranean termite), *Reticulitermes santonensis, Reticulitermes speratus, Reticulitermes tibialis, Reticulitermes virginicus, Schedorhinotermes* spp., and *Zootermopsis* spp. (rotten-wood termites).

In additional embodiments, the method of the present disclosure may be used to control members of the Order Lepidoptera (moths and butterflies) including, but not limited to, *Chilo suppressalis* (rice striped stem borer), *Alabama argillacea* (cotton leafworm), *Achoea janata, Adoxophyes* spp., *Adoxophyes orana, Agrotis* spp. (cutworms), *Agrotis ipsilon* (black cutworm), *Amorbia cuneana, Amyelosis transitella* (navel orangeworm), *Anacamptodes defectaria, Anarsia lineatella* (peach twig borer), *Anomis sabulifera* (jute looper), *Anticarsia gemmatalis* (velvetbean caterpillar), *Archips argyrospila* (fruittree leafroller), *Archips rosana* (rose leafroller), *Argyrotaenia* spp. (tortricid moths), *Argyrotaenia citrana* (orange tortrix), *Autographa gamma, Bonagota cranaodes, Borbo cinnara* (rice leaf folder), *Bucculatrix thurberiella* (cotton leafperforator), *Caloptilia* spp. (leaf miners), *Capua reticulana, Carposina niponensis* (peach fruit moth), *Chilo* spp. (stem borers), *Chilo suppressalis, Chilo polychrysus, Chlumetia transversa* (mango shoot borer), *Choristoneura rosaceana* (obliquebanded leafroller), *Chrysodeixis* spp., *Cnaphalocerus medinalis* (grass leafroller), *Colias* spp., *Conpomorpha cramerella, Cossus cossus* (carpenter moth), *Crambus* spp. (Sod webworms), *Cydiafunebrana* (plum fruit moth), *Cydia molesta* (oriental fruit moth), *Cydia nignicana* (pea moth), *Cydia pomonella* (codling moth), *Darna diducta, Diaphania* spp. (stem borers), *Diatraea* spp. (stalk borers), *Diatraea saccharalis* (sugarcane borer), *Diatraea graniosella* (southwester corn borer), *Earias* spp. (bollworms), *Earias insulata* (Egyptian bollworm), *Earias vitella* (rough northern bollworm), *Ecdytopopha aurantianum, Elasmopalpus lignosellus* (lesser cornstalk borer), *Epiphysias postruttana* (light brown apple moth), *Ephestia* spp. (flour moths), *Ephestia cautella* (almond moth), *Ephestia elutella* (tobbaco moth), *Ephestia kuehniella* (Mediterranean flour moth), *Epimeces* spp., *Epinotia aporema, Erionota thrax* (banana skipper), *Eupoecilia ambiguella* (grape berry moth), *Euxoa auxiliaris* (army cutworm), *Feltia* spp. (cutworms), *Gortyna* spp. (stem borers), *Grapholita molesta* (oriental fruit moth), *Hedylepta indicata* (bean leaf webber), *Helicoverpa* spp. (noctuid moths), *Helicoverpa armigera* (cotton bollworm), *Helicoverpa zea* (bollworm/corn earworm), *Heliothis* spp. (noctuid moths), *Heliothis virescens* (tobacco budworm), *Hellula undalis* (cabbage webworm), *Indarbela* spp. (root borers), *Keiferia lycopersicella* (tomato pinworm), *Leucinodes orbonalis* (eggplant fruit borer), *Leucoptera malifoliella, Lithocollectis* spp., *Lobesia botrana* (grape fruit moth), *Loxagrotis* spp. (noctuid moths), *Loxagrotis albicosta* (western bean cutworm), *Lymantria dispar* (gypsy moth), *Lyone-*

*tia clerkella* (apple leaf miner), *Mahasena corbetti* (oil palm bagworm), *Malacosoma* spp. (tent caterpillars), *Mamestra brassicae* (cabbage armyworm), *Maruca testulalis* (bean pod borer), *Metisa plana* (bagworm), *Mythimna unipuncta* (true armyworm), *Neoleucinodes elegantalis* (small tomato borer), *Nymphula depunctalis* (rice caseworm), *Operophthera brumata* (winter moth), *Ostrinia nubilalis* (European corn borer), *Oxydia vesulia, Pandemis cerasana* (common currant tortrix), *Pandemis heparana* (brown apple tortrix), *Papilio demodocus, Pectinophora gossypiella* (pink bollworm), *Peridroma* spp. (cutworms), *Peridroma saucia* (variegated cutworm), *Perileucoptera coffeella* (white coffee leafminer), *Phthorimaea operculella* (potato tuber moth), *Phyllocnisitis citrella, Phyllonolycter* spp. (leafminers), *Pieris rapae* (imported cabbageworm), *Plathypena scabra, Plodia interpunctella* (Indian meal moth), *Plutella xylostella* (diamondback moth), *Polychrosis viteana* (grape berry moth), *Prays endocarpa, Prays oleae* (olive moth), *Pseudaletia* spp. (noctuid moths), *Pseudaletia unipunctata* (true armyworm), *Pseudoplusia includens* (soybean looper), *Rachiplusia nu, Scirpophaga* spp. (stem borers), *Scirpophaga incertulas, Scirpophaga innotata, Sesamia* spp. (stem borers), *Sesamia inferens* (pink rice stem borer), *Sesamia nonagrioides, Setora nitens, Sitotroga cerealella* (Angoumois grain moth), *Sparganothis pilleriana, Spodoptera* spp. (armyworms), *Spodoptera exigua* (beet armyworm), *Spodoptera frugiperda* (fall armyworm), *Spodoptera eridania* (southern armyworm), *Synanthedon* spp. (root borers), *Thecla basilides, Anticarsia* [*Thermisia*] *gemmatalis, Tineola bisselliella* (webbing clothes moth), *Trichoplusia ni* (cabbage looper), *Tuta absoluta, Yponomeuta* spp., *Zeuzera coffeae* (red branch borer), and *Zeuzera pyrina* (leopard moth). In at least some embodiments, the method of the present disclosure may be used to control *Spodoptera exigua*.

The method of the present disclosure may be used to also control members of the Order Mallophaga (chewing lice) including, but not limited to, *Bovicola ovis* (sheep biting louse), *Menacanthus stramineus* (chicken body louse), and *Menopon gallinea* (common hen louse).

In additional embodiments, the method of the present disclosure may be used to control members of the Order Orthoptera (grasshoppers, locusts, and crickets) including, but not limited to, *Anabrus simplex* (Mormon cricket), *Gryllotalpidae* (mole crickets), *Locusta migratoria, Melanoplus* spp. (grasshoppers), *Microcentrum retinerve* (angularwinged katydid), *Pterophylla* spp. (kaydids), *chistocerca gregaria, Scudderia furcata* (forktailed bush katydid), and *Valanga nigricorni*.

In other embodiments, the method of the present disclosure may be used to control members of the Order Phthiraptera (sucking lice) including, but not limited to, *Haematopinus* spp. (cattle and hog lice), *Linognathus ovillus* (sheep louse), *Pediculus humanus capitis* (human body louse), *Pediculus humanus humanus* (human body lice), and *Pthirus pubis* (crab louse).

In particular embodiments, the method of the present disclosure may be used to control members of the Order Siphonaptera (fleas) including, but not limited to, *Ctenocephalides canis* (dog flea), *Ctenocephalides felis* (cat flea), and *Pulex irritans* (human flea).

In other embodiments, the method of the present disclosure may be used to control members of the Order Thysanoptera (thrips) including, but not limited to, *Caliothrips fasciatus* (bean thrips), *Caliothrips phaseoli, Frankliniella fusca* (tobacco thrips), *Frankliniella occidentalis* (western flower thrips), *Frankliniella shultzei, Frankliniella williamsi* (corn thrips), *Heliothrips haemorrhaidalis* (greenhouse thrips), *Riphiphorothrips cruentatus, Scirtothrips* spp., *Scirtothrips citri* (citrus thrips), *Scirtothrips dorsalis* (yellow tea thrips), *Taeniothrips rhopalantennalis, Thrips* spp., *Thrips tabaci* (onion thrips), and *Thrips hawaiiensis* (Hawaiian flower thrips).

The method of the present disclosure may be used to also control members of the Order Thysanura (bristletails) including, but not limited to, *Lepisma* spp. (silverfish) and *Thermobia* spp. (firebrats).

In further embodiments, the method of the present disclosure may be used to control members of the Order Acari (mites and ticks) including, but not limited to, *Acarapsis woodi* (tracheal mite of honeybees), *Acarus* spp. (food mites), *Acarus siro* (grain mite), *Aceria mangiferae* (mango bud mite), *Aculops* spp., *Aculops lycopersici* (tomato russet mite), *Aculops pelekasi, Aculus pelekassi, Aculus schlechtendali* (apple rust mite), *Amblyomma americanum* (lone star tick), *Boophilus* spp. (ticks), *Brevipalpus obovatus* (privet mite), *Brevipalpus phoenicis* (red and black flat mite), *Demodex* spp. (mange mites), *Dermacentor* spp. (hard ticks), *Dermacentor variabilis* (american dog tick), *Dermatophagoides pteronyssinus* (house dust mite), *Eotetranycus* spp., *Eotetranychus carpini* (yellow spider mite), *Epitimerus* spp., *Eriophyes* spp., *Ixodes* spp. (ticks), *Metatetranycus* spp., *Notoedres cati, Oligonychus* spp., *Oligonychus coffee, Oligonychus ilicus* (southern red mite), *Panonychus* spp., *Panonychus citri* (citrus red mite), *Panonychus ulmi* (European red mite), *Phyllocoptruta oleivora* (citrus rust mite), *Polyphagotarsonemun latus* (broad mite), *Rhipicephalus sanguineus* (brown dog tick), *Rhizoglyphus* spp. (bulb mites), *Sarcoptes scabiei* (itch mite), *Tegolophus perseaflorae, Tetranychus* spp., *Tetranychus urticae* (twospotted spider mite), and *Varroa destructor* (honey bee mite).

In additional embodiments, the method of the present disclosure may be used to control members of the Order Nematoda (nematodes) including, but not limited to, *Aphelenchoides* spp. (foliar nematodes), *Belonolaimus* spp. (sting nematodes), *Criconemella* spp. (ring nematodes), *Dirofilaria immitis* (dog heartworm), *Ditylenchus* spp. (stem and bulb nematodes), *Heterodera* spp. (cyst nematodes), *Heterodera zeae* (corn cyst nematode), *Hirschmanniella* spp. (root nematodes), *Hoplolaimus* spp. (lance nematodes), *Meloidogyne* spp. (root knot nematodes), *Meloidogyne incognita* (root knot nematode), *Onchocerca volvulus* (hook-tail worm), *Pratylenchus* spp. (lesion nematodes), *Radopholus* spp. (burrowing nematodes), and *Rotylenchus reniformis* (kidney-shaped nematode).

In at least some embodiments, the method of the present disclosure may be used to control at least one insect in one or more of the Orders Lepidoptera, Coleoptera, Hemiptera, Thysanoptera, Isoptera, Orthoptera, Diptera, Hymenoptera, and Siphonaptera, and at least one mite in the Order Acari.

In some embodiments, a method of protecting rice from infestation and attack by pests comprises contacting rice with a pesticidal composition that comprises a synergistically effective amount of spinetoram and methoxyfenozide, wherein the pests comprise at least one lepidoptera pests.

In one particular embodiment, a method of protecting rice from infestation and attack by pests comprises contacting rice with a pesticidal composition that comprises a synergistically effective amount of spinetoram and methoxyfenozide, wherein the pests comprise rice striped stem borer, *Chilo suppressalis*.

In further embodiments, the method of protecting a plant from infestation and attack by pests comprises contacting the plant with a pesticidal composition comprising a synergistically effective amount of spinetoram and methoxyfenozide, wherein the pests comprise lepidoptera pests selected from the group consisting of: striped stem borer (*Chilo suppressalis*), dark-headed stemborer (*Chilo polychrysus*), yellow stem borer (*Scirpophaga incertulas*), white stemborer (*Scirpophaga innotata*), pink stem borer (*Sesamia inferens*), codling moth (*Cydia pomonella*), navel orangeworm (*Amyelois transitella*), peach twig borer (*Anarsia lineatella*), oriental fruit moth (*Grapholita molesta*), omnivorous leafroller (*Platynota stultana*), soybean looper (*Chrysodeixis [Pseudoplusia] includens*), tobacco budworm (*Heliothis virescens*), oblique-banded leafroller (*Choristoneura rosaceana*), cotton leafworm (*Alabama argillacea*), rice leafroller (*Cnaphalocrocis medinalis*), fruittree leafroller (*Archips argyrospila*), cotton bollworms (*Helicoverpa armigera, Helicoverpa zea*), beet armyworm (*Spodoptera exigua*), *Adoxophyes orana*, and diamondback moth, (*Plutella xylostella*).

In still further embodiments, the method of protecting a plant from infestation and attack by pests comprises contacting the plant with a pesticidal composition comprising a synergistically effective amount of spinetoram and methoxyfenozide, wherein the pests comprise lepidoptera pests and the plants is selected from the group consisting of rice, soybean, cotton, tree fruit and nut crops and vine crops.

Accordingly, a pesticidal composition comprises spinetoram and methoxyfenozide in an amount of at least 3 parts by weight per 1 part by weight of spinetoram. The pesticidal composition shows a synergistic activity against at least one lepidoptera pests.

In some particular embodiments, the pesticidal composition comprises methoxyfenozide in an amount of at least 4.5 parts by weight per 1 part by weight of spinetoram.

In further embodiments, the pesticidal composition comprises spinetoram and methoxyfenozide in a weight ratio of between about 1:3 and about 1:10.

In particular embodiments, the pesticidal composition comprises spinetoram and methoxyfenozide in a weight ratio of between about 1:4.5 and about 1:5.5

In one embodiment of present disclosure, the pesticidal composition may be used in conjunction (such as, in a compositional mixture, or a simultaneous or sequential application) with one or more compounds having acaricidal, algicidal, avicidal, bactericidal, fungicidal, herbicidal, insecticidal, molluscicidal, nematicidal, rodenticidal, and/or virucidal properties.

In another embodiment of present disclosure, the pesticidal composition may be used in conjunction (such as, in a compositional mixture, or a simultaneous or sequential application) with one or more compounds that are antifeedants, bird repellents, chemosterilants, herbicide safeners, insect attractants, insect repellents, mammal repellents, mating disrupters, plant activators, plant growth regulators, and/or synergists.

The pesticidal compositions of present disclosure show a synergistic effect, providing superior pest control at lower pesticidally effective amounts of the combined active compounds than when of spinetoram or methoxyfenozide is used alone.

The pesticidal compositions of present disclosure may have high synergistic pest control and allow for a lower effective dosage rate, an increased environmental safety, and a reduced incidence of pest resistance.

The following examples serve to explain embodiments of the present invention in more detail. These examples should not be construed as being exhaustive or exclusive as to the scope of this disclosure.

EXAMPLES

Determination of the Existence of Synergic Effect

Cotoxicity Coefficient (CTC) value was used to determine an existence of synergic effect between spinetoram and methoxyfenozide in the formulated pesticidal composition.

The CTC value, which is based on the lethal concentration and the proportion of each pesticidal compounds (spinetoram, methoxyfenozide) in the formulated composition, was calculated using the following equation:

$$CTC=[\text{Actual Toxicity Index of Composition} \div \text{Theoretical Toxicity Index of Composition}] \times 100,$$

wherein

Toxicity Index of Spinetoram=100,

Toxicity Index of Methoxyfenozide=[$LC_{50}$ of Spinetoram $LC_{50}$ of Methoxyfenozide]×100, Measured Toxicity Index of Composition=[$LC_{50}$ of Spinetoram $LC_{50}$ of Composition]×100, and Theoretical Toxicity Index of Composition=[Toxicity Index of Spinetoram×% wt of Spinetoram in Composition]+[Toxicity Index of Methoxyfenozide×% wt of Methoxyfenozide].

The CTC value of the formulated composition was used to determine the biological responses to the treatment: additive, synergism, or antagonism. The CTC value of more than 120 indicates a synergistic effect between the combined pesticidal compounds. The CTC value of about 80 to 120 indicates an additive effect between the combined pesticidal compounds. The CTC value of less than 80 indicates antagonistic effect between the combined pesticidal compounds Synergistic Effect of Spinetoram and Methoxyfenozide Against Against Striped Stem Borer (SSB) on Rice Pesticidal compositions were prepared by thoroughly mixing spinetoram and methoxyfenozide at various weight ratios as shown in TABLE 3.

TABLE 3

| Compsoition No. | Weight Ratio of Spinetoram to Methoxyfenozide |
|---|---|
| 1 | 1:1 |
| 2 | 1:3 |
| 3 | 1:5 |
| 4 | 1:7 |
| 5 | 1:9 |

The effectiveness of the pesticidal compositions for controlling of striped stem borer on rice was determined using laboratory bioassays, and compared to those of three controls. In the first control, only spinetoram was used for the treatment. In the second control, only methoxyfenozide was used for the treatment. In the third control, no pesticide was used.

The rice stem dipping method based on Standard Method for Bioassay Test (Chinese Standard Method NY/T1154.4-2006: Continuous Immersion Test for Insecticide Systemic Activity) was used to conduct the laboratory bioassays.

Five stems of rice were dipped into the solutions of pestidical compositions for 10 seconds and then taken out for drying in the air. The treated stems were placed into glass tubes. Treatment with water, solvent, and emulsifier alone was used as reference check. There were four replicates for each treatment. About 10±1 larvae of third-instar striped stem borer were placed into each glass tube. The openings of the tubes were covered with gauze. Laboratory bioassays were conducted at room temperature. The number of dead larvae was recorded at 72 hours following the treatment. The larvae were judged as dead when they did not respond to a slightly contact using forceps. The mortality, toxicity regression equation, correlation coefficient (r), $LC_{50}$, and 95% confidence intervals were calculated based on the data.

The experimental results were as shown in TABLE 4 and TABLE 5.

TABLE 4

Laboratory Insecticidal Activities of Spinetoram, Methoxyfenozide, and Disclosed Pesticidal Compositions Against Striped Stem Borer (SSB) on Rice

| Treatment | Mass Concentration (mg/L) | Numbers of Tested SSB | Numbers of Dead SSB | Mortality (%) |
|---|---|---|---|---|
| Untreated | 0 | 10 | 0 | 0 |
| Spinetoram (S) | 4 | 10.25 | 9.75 | 95.23 |
|  | 2 | 10.5 | 8.5 | 81.14 |
|  | 1 | 10.5 | 6.75 | 64.09 |
|  | 0.5 | 10.5 | 4 | 37.73 |
|  | 0.25 | 10.75 | 2 | 18.41 |
|  | 0.125 | 10.75 | 0.5 | 4.55 |
| Methoxyfenozide (M) | 80 | 10 | 8.75 | 87.50 |
|  | 40 | 10 | 6.75 | 67.50 |
|  | 20 | 10.25 | 7 | 43.86 |
|  | 10 | 10.5 | 3 | 28.41 |
|  | 5 | 11 | 1.5 | 13.64 |
|  | 2.5 | 10.25 | 0.5 | 4.77 |
| Composition 1, S:M (1:1) | 4 | 10.75 | 10 | 92.96 |
|  | 2 | 10.25 | 7.25 | 70.68 |
|  | 1 | 10.25 | 5.25 | 51.14 |
|  | 0.5 | 10.75 | 3.25 | 30.23 |
|  | 0.25 | 10.5 | 1 | 9.54 |
|  | 0.125 | 10 | 0 | 0 |
| Composition 2, S:M (1:3) | 8 | 10.25 | 9.25 | 90.46 |
|  | 4 | 10 | 6.75 | 67.50 |
|  | 2 | 10.5 | 5.5 | 52.50 |
|  | 1 | 10.5 | 3.5 | 33.41 |
|  | 0.5 | 10 | 2 | 20.00 |
|  | 0.25 | 10.25 | 0.75 | 7.27 |
| Composition 3, S:M (1:5) | 8 | 10 | 9 | 90.00 |
|  | 4 | 10.5 | 7.25 | 69.09 |
|  | 2 | 10 | 4.5 | 45.00 |
|  | 1 | 10.25 | 2.25 | 21.82 |
|  | 0.5 | 10 | 0.5 | 5.00 |
|  | 0.25 | 10 | 0 | 0 |
| Composition 4, S:M (1:7) | 20 | 10 | 10 | 100 |
|  | 10 | 10 | 8.75 | 87.50 |
|  | 5 | 10 | 6 | 60.00 |
|  | 2.5 | 10.25 | 3.75 | 36.59 |
|  | 1.25 | 10 | 2 | 20.00 |
|  | 0.625 | 10.25 | 0.5 | 4.77 |
| Composition 5, S:M (1:9) | 20 | 10 | 9.5 | 95.00 |
|  | 10 | 10 | 8 | 80.00 |
|  | 5 | 10 | 5.75 | 57.50 |
|  | 2.5 | 10 | 3.5 | 35.00 |
|  | 1.25 | 10 | 1 | 10.00 |
|  | 0.625 | 10 | 0 | 0 |

TABLE 5

Calculation of Laboratory Insecticidal Activities of Spinetoram, Methoxyfenozide, and Disclosed Pesticidal Compositions against Striped Stem Borer (SSB) on Rice

| Treatment | $LC_{50}$ (mg/L) | $LC_{90}$ (mg/L) | CTC |
|---|---|---|---|
| Spinetoram (S) | 0.71 (0.65-0.77) | 2.76 (2.41-3.17) | — |
| Methoxyfenozide (M) | 21.05 (18.59-23.82) | 107.74 (84.59-134.66) | — |
| Composition 1, S:M (1:1) | 0.96 (0.79-1.15) | 3.64 (2.66-4.99) | 143.09 |
| Composition 2, S:M (1:3) | 1.73 (1.41-2.11) | 9.53 (6.57-13.81) | 149.08 |
| Composition 3, S:M (1:5) | 2.32 (2.09-2.58) | 8.07 (6.75-9.65) | 157.12 |
| Composition 4, S:M (1:7) | 3.37 (2.80-4.06) | 12.62 (8.96-17.79) | 136.35 |
| Composition 5, S:M (1:9) | 4.10 (3.61-4.67) | 14.39 (11.95-17.33) | 132.84 |

TABLE 6

Effectiveness and Synergistic Effects of Pesticidal Compositions Against Striped Stem Borer

| Treatment | Weigth Ratio of Spinetoram:Methoxyfenozide | Cotoxicity Coefficient (CTC) |
|---|---|---|
| Untreated | — | — |
| Spinetoram (S) | — | — |
| Methoxyfenozide (M) | — | — |
| Composition 1 | 1:1 | 143.09 |
| Composition 2 | 1:3 | 149.08 |
| Composition 3 | 1:5 | 157.12 |
| Composition 4 | 1:7 | 136.35 |
| Composition 5 | 1:9 | 132.84 |

As shown in TABLE 6, the CTC values of Compositions 1-5 were found to be above 120. These results indicated strong synergistic effects between spinetoram and methoxyfenozide for activities against striped stem borer on rice. Among them, Composition 3 with the weight ratio of spinetoram:methoxyfenozide of 1:5 showed the strongest synergistic effect against striped stem borer, *Chilo suppressalis*.

While the present disclosure may be susceptible to various modifications and alternative forms, specific embodiments have been described by way of example in detail herein. However, it should be understood that the present disclosure is not intended to be limited to the particular forms disclosed. Rather, the present disclosure is to cover all modifications, equivalents, and alternatives falling within the scope of the present disclosure as defined by the following appended claims and their legal equivalents.

We claim:

1. A method of protecting rice from infestation and attack by *Chilo suppressalis*, the method comprising:

contacting rice with a pesticidal composition to provide a synergistic effect against *C. suppressalis*, wherein the pesticidal composition comprises spinetoram and methoxyfenozide in a weight ratio of spinetoram to methoxyfenozide of between 1:1 and 1:10.

2. The method of claim 1, wherein the pesticidal composition comprises spinetoram and methoxyfenozide in a weight ratio of spinetoram to methoxyfenozide of between 1:1 and 1:9.

3. The method of claim 1, wherein the pesticidal composition comprises spinetoram and methoxyfenozide in a weight ratio of spinetoram to methoxyfenozide of between 1:3 and 1:10.

4. The method of claim 1, wherein the pesticidal composition comprises spinetoram and methoxyfenozide in a weight ratio of spinetoram to methoxyfenozide of between 1:4.5 and 1:5.5.

5. The method of claim 1, wherein the pesticidal composition further comprises a phytologically-acceptable inert carrier.

6. The method of claim 1, wherein the pesticidal composition further comprises an additive selected from a surfactant, a stabilizer, an emetic agent, a disintegrating agent, an antifoaming agent, a wetting agent, a dispersing agent, a binding agent, dye, filler, or combinations thereof.

7. The method of claim 1, wherein the pesticidal composition comprises spinetoram and methoxyfenozide in a weight ratio of spinetoram to methoxyfenozide of between 1:4.5 and 1:10.

8. The method of claim 7, wherein the pesticidal composition comprises spinetoram and methoxyfenozide in a weight ratio of spinetoram to methoxyfenozide of between 1:4.5 and 1:9.

9. A method for effectively controlling striped stem borer infestation with a lower dosage rate of methoxyfenozide, the method comprising:
applying methoxyfenozide to an area infested by striped stem borer insects, wherein the methoxyfenozide is applied in conjunction with spinetoram in a weight ratio of spinetoram to methoxyfenozide of between 1:1 and 1:10,
thereby killing at least 90% of the striped stem borer insects in the area.

10. The method according to claim 9, wherein the methoxyfenozide is applied in conjunction with spinetoram in a weight ratio of spinetoram to methoxyfenozide of between 1:3 and 1:10.

11. The method according to claim 9, wherein the methoxyfenozide is applied in conjunction with spinetoram in a weight ratio of spinetoram to methoxyfenozide of between 1:4.5 and 1:5.5.

12. The method according to claim 9, wherein the methoxyfenozide is applied simultaneously with spinetoram in a mixture of the methoxyfenozide and the spinetoram.

13. The method according to claim 9, wherein the methoxyfenozide is applied in conjunction with spinetoram to an area comprising rice plants.

14. The method according to claim 13, wherein the methoxyfenozide is applied in conjunction with spinetoram to a rice crop.

15. The method according to claim 9, wherein the methoxyfenozide is applied in conjunction with spinetoram in an amount of 18 mg/L methoxyfenozide or less.

16. The method according to claim 15, wherein the methoxyfenozide is applied in conjunction with spinetoram in an amount between 6.67 mg/L and 18 mg/L methoxyfenozide.

\* \* \* \* \*